(12) United States Patent
Korsgren et al.

(10) Patent No.: US 9,446,066 B2
(45) Date of Patent: Sep. 20, 2016

(54) METHODS FOR REDUCING PULMONARY UPTAKE OF INTRAVENOUSLY INJECTED CELLS

(75) Inventors: Olle Korsgren, Uppsala (SE); Bo Nilsson, Uppsala (SE)

(73) Assignee: TX MEDIC AB, Viken (SE)

( * ) Notice: Subject to any disclaimer, the term of this patent is extended or adjusted under 35 U.S.C. 154(b) by 0 days.

(21) Appl. No.: 13/810,425

(22) PCT Filed: Jul. 8, 2011

(86) PCT No.: PCT/SE2011/050928
§ 371 (c)(1),
(2), (4) Date: Jan. 15, 2013

(87) PCT Pub. No.: WO2012/008908
PCT Pub. Date: Jan. 19, 2012

(65) Prior Publication Data
US 2013/0115200 A1 May 9, 2013

Related U.S. Application Data

(60) Provisional application No. 61/364,994, filed on Jul. 16, 2010.

(51) Int. Cl.
*A61K 35/26* (2015.01)
*A61K 31/737* (2006.01)

(52) U.S. Cl.
CPC ............. *A61K 31/737* (2013.01); *A61K 35/26* (2013.01)

(58) Field of Classification Search
None
See application file for complete search history.

(56) References Cited

U.S. PATENT DOCUMENTS

| 5,605,938 A * | 2/1997 | Roufa et al. | 514/59 |
| 8,906,884 B2 | 12/2014 | Nilsson et al. | |
| 2006/0111319 A1 * | 5/2006 | Nilsson et al. | 514/59 |

FOREIGN PATENT DOCUMENTS

EP 0375976 A2 7/1990

OTHER PUBLICATIONS

Ballen, Karen K; et al; "Autologous Stem-Cell Transplantation Can Be Performed Safely Without the Use of Blood-Product Support" Journal of Clinical Oncology, 22, 4087-4094, 2004.*
Bergqvist, D; "Posteroperative Thromboemoblism: Frequency, Etiology, Prophylaxis" Springer-Verlag, New York, 1983.*
Raghavachar, A; "Progenitor Cell (CFUc) Reconstitution After Autologous Stem Cell Transfusion in Lethally Irradiated Dogs: Decreased CFUc Populations in Blood and Bone Marrow Correlate with the Fraction Mobilizable by Dextran Sulphate" Experimental Hematology, 11, 996-1004, 1983.*
Illum, L; et al; "Effect of a Selected Suppression of the Reticuloendothelial System on the Distribution of Model Carrier Particles" Journal of Pharmaceutical Science, 75, 16-22, 1986.*
Fiorante, Patrizia; et al; "Low molecular weight dextran sulfate prevents complement activation and delays hyperacute rejection in pig-to-human xenotransplantation models" Xenotransplantation, 8, 24-35, 2001.*
Bergentz, Sven-Erik; "Dextran in the Prophylaxis of Pulmonary Embolism" World Journal of Surgery, 2, 19-25, 1978.*
Bellavia, Angelo; et al; "Effects of Dextran Sulphate on Lymphoblast Extravasation into inflammatory skin sites" Immunopharmacology, 13, 173-180, 1987.*
Furlani, Dario; et al; "Is the intravascular administration of mesenchymal stem cells safe? Mesenchymal stem cells and intravital microscopy" Microvascular Research, 77, 370-376, 2009.*
Rodriguez, Horacia; et al; "Total Pancreatectomy and Autologous Islet Cell Transplantation as a Means to Treat Severe Chronic Pancreatitis" Journal of Gastrointestinal Surgery, 7, 978-989, 2003.*
Eriksson et al, Position Emission Tomography in Clinical Islet Transplantation, American Journal of Transplantation, 2009, 9: 2816-2824.
Eich et al, Visualization of Early Engraftment in Clinical Islet Transplantation by Positron-Emission Tomography, New England Journal of Medicine, 2007, 356;26; p. 2754-2755.
Illum, et al, Effect of a Selected Suppression of the Reticuloendothelial System on the Distribution of Model Carrier Particles, Journal of Pharmaceutical Sciences, vol. 75, No. 1, Jan. 1986.
Hayakawa et al, Dextran Sulfate and Stromal Cell Derived Factor-1 Promote CXCR4 Expression and Improve Bone Marros Homing Efficiency of Infused Hematopoietic Stem Cells, J Nippon Med Sch, 2009; 76(4), p. 198-208.
Dixon et al, Adherence of adoptively transferred alloreactive Th1 cells in lung: partial dependence on LFA-1 and ICAM-1, Am J Physiol Lung Cell Mol Physiol, 279: L583-L591, 2000.
Eich et al, Positron Emission Tomography: A Real-Time Tool to Quantify Early Islet Engraftment in a Preclinical Large Animal Model, Transplantation, vol. 84, No. 7, Oct. 15, 2007, p. 893-898.
European Search Report, dated Jul. 3, 2015 from corresponding European Application No. 11807152.1.

(Continued)

*Primary Examiner* — Renee Claytor
*Assistant Examiner* — David Berke-Schlessel
(74) *Attorney, Agent, or Firm* — Porter Wright Morris & Arthur LLP

(57) ABSTRACT

Dextran sulfate is used in order to reduce pulmonary uptake of intravenously injected Dextran sulfate is capable of reducing the pulmonary uptake of the intravenously injected cells to the levels obtained for intraarterial injection of the cells but without the accompanying risks and side effects of using intraarterial cell injection. The dextran sulfate can therefore be used in a composition together with tumor infiltrating T-lymphocytes to treat metastatic cancer in a subject.

19 Claims, 2 Drawing Sheets

(56) References Cited

OTHER PUBLICATIONS

Millard et al., Inhibition of Direct and Indirect TLR-Mediated Activation of Human NK Cells by Low Molecular Weight Dextran Sulfate, Molecular Immunology, vol. 47, pp. 2349-2358 (Available online Jun. 11, 2010).

Patel et al., Suppression of Liver Uptake of Liposomes by Dextran Sulfate 500, Proc. Natl. Acad. Sci. USA, vol. 80, pp. 6518-6522 (Nov. 1983).

Deckers et al., RNA-Mediated Transfer of Tumor Immunity—A New Model for the Immunotherapy of Cancer, vol. 28, No. 5, pp. 1219-1228 (Nov. 1971).

Ravaud et al., Repeated Tumor Infiltrating Lymphocytes (TIL) Infusion in Metastatic Malignant Melanoma (MMM), European Journal of Cancer, vol. 29, p. S180 (Jan. 1, 1993).

Pulmonary Embolism, http://www.mayoclinic.org/diseases-conditions/pulmonary-embolism/basics/definition/con-20022849, downloaded Feb. 28, 2016.

Saunders, "Clot", Miller-Keane Encyclopedia and Dictionary of Medicine, Nursing, and Allied Health, Seventh Edition, 2003, Elsevier, Inc., from http://medical-dictionary.thefreedictionary.com/clot, downloaded Feb. 28, 2016.

Barbash et al, Circulation, 108:863-868 (2003).
Gao et al, Cells Tissues Organs, 169:12-20 (2001).
Noort et al, Experimental Hematology, 30:870-878 (2002).
Editor, Canad. M. A. J., 76:139 (1957).
Hall et al, J. Clin Path., 5:366 (1952).

* cited by examiner

METHODS FOR REDUCING PULMONARY UPTAKE OF INTRAVENOUSLY INJECTED CELLS

TECHNICAL FIELD

The present invention generally relates to administration of cells and to techniques for preventing unwanted uptake of intravenously injected cells in the lungs.

BACKGROUND

Adoptive immunotherapy for metastatic cancer refers to the autologous or allogeneic transfer of immune cells capable of mediating an anti-tumor effect on tumor-bearing host. Tumor infiltrating T lymphocytes (TILs) are isolated from tumor tissue and characterized and expanded ex vivo and are re-infused into the cancer patients. Up to $10^9$ activated cells are infused after a lymphodepleting regimen along with growth factors to augment the in vivo effects of transferred cells. In patients with advanced metastatic melanoma, refractory to other treatments, 50% have demonstrated an objective response according to the Response Evaluation Criteria in Solid Tumors (RECIST) which is based on radiological measurements of lesion size.

The difficulty in evaluating cell trafficking and distribution of transferred cells in vivo is one of the major concerns in adoptive therapy. Radioisotope cell labeling is the most common method used to study the distributions of cells in vivo. $^{18}$F-2-fluoro-2-deoxy-D-glucose ([$^{18}$F]FDG) has been extensively used as a parameter of glucose metabolism in various cells allowing in vivo visualization of cells and tissues by Positron Emission Tomography (PET) [3]. Labeling studies of blood components demonstrate that erythrocytes and leukocytes incorporate and maintain [$^{18}$F]FDG for several hours.

SUMMARY

The present embodiments generally relates to administration of cells and to techniques for preventing unwanted uptake of intravenously injected cells in the lungs.

Aspects of the embodiments relate to dextran sulfate for use in reducing pulmonary uptake of intravenously injected cells and to a method of reducing pulmonary uptake of intravenously injected cells in a human or animal body by administering dextran sulfate to the human or animal body.

Autologous or allogeneic transfer of tumor infiltrating T-lymphocytes is a promising treatment for metastatic cancers, but a major concern is the difficulty in evaluating cell trafficking and distribution in adoptive cell therapy. This document presents a method of tracking transfusion of T-lymphoblasts in a porcine model by [$^{18}$F]FDG and Positron Emission Tomography.

T-lymphoblasts were labeled with the positron emitting tracer [$^{18}$F]FDG through incubation. The T-lymphoblasts were administered into the bloodstream and the distribution was followed by Positron Emission Tomography (PET) for 120 minutes. The cells were administered either intravenously into the internal jugular vein (n=5) or intraarterially into the ascending aorta (n=1). Two of the pigs given intravenous administration were pretreated with dextran sulfate.

The cellular kinetics and distribution was readily quantifiable for up to 120 minutes. High (78.6% of the administered cells) heterogeneous pulmonary uptake was found after completed intravenous transfusion. The pulmonary uptake was decreased either by pre-incubating and coadministrating the T-lymphoblasts with dextran sulfate, or by administrating them intraarterially.

Aspects of the embodiments relates to a composition comprising dextran suflate and tumor infiltrating T-lymphocytes provided in a pharmaceutically acceptable fluid or liquid carrier. This composition is useful in treating metastatic cancer in a subject.

The present work shows the feasibility of quantitatively monitoring and evaluating cell trafficking and distribution following administration of [18F]FDG-labelled T-lymphoblasts. The protocol can potentially be transferred to the clinical setting with few modifications.

BRIEF DESCRIPTION OF THE DRAWINGS

The invention, together with further objects and advantages thereof, may best be understood by making reference to the following description taken together with the accompanying drawings, in which.

DETAILED DESCRIPTION

Figure 1:
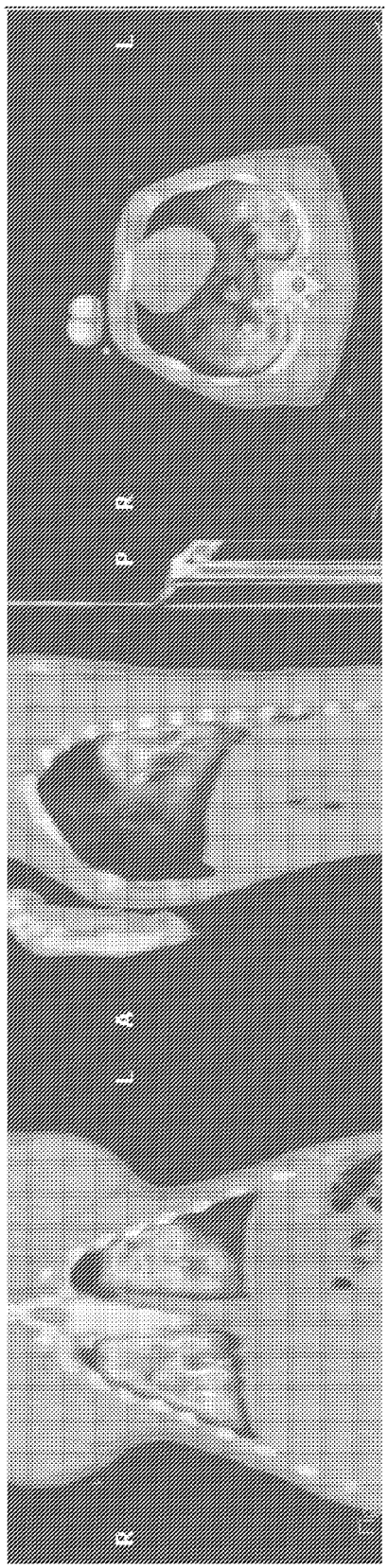
FIG. 1 illustrates lung distribution of [$^{18}$F]FDG-labeled T-lymphoblasts 30 minutes after intravenous administration. From left to right: coronal, sagittal and transaxial views. Color denotes cellular density ranging between 0-106 cells/cc.

The present embodiments generally relate to the usage of dextran sulfate (DS) for inhibiting or at least reducing pulmonary uptake and accumulation of intravenously administered cells.

Cell therapy can find application in vastly different areas of medical treatment in the human and animal, preferably mammalian, body. For instance, cell therapy, where T-lymphocytes or other immunoregulatory cells are administered, is a promising treatment for metastatic cancers. Such cells could generally be administered either intravenously or intraarterially. Intraarterial injections of cells are, though, generally not preferred due to the risk of damaging the artery, with severe bleeding risks and accompanying complications. Hence, intravenous injection of cells is generally preferred. However and as is further illustrated herein, intravenous injection of cells typically result in a high pulmonary uptake and accumulation of the injected cells in the lungs. This is most often not advantageously unless the cells are destined to the lungs. Hence, a vast amount, typically about 80%, of the intravenously injected cells will be taken up in the lungs and therefore do not contribute to the desired therapeutic effect of the cells.

The inventors have surprisingly discovered that dextran sulfate can be used to reduce this pulmonary uptake in connection with intravenous injection of cells. The treatment with dextran sulfate will in fact reduce the pulmonary uptake to levels that occur in connection with intraarterial injections but without the health risks associated with intraarterial injections.

The present embodiments can be used in connection with any intravenous injections of cells regardless of origin and cell type. The embodiments can therefore be used both in connection with autologous, allogenic or xenogenic injection of cells but is particularly suitable for autologous or allogenic intravenous injection of cells.

Non-limiting examples of cell types that can be injected and to which the present embodiments can be applied include stem cells, such as hematopoietic stem cells, mesenchymal stem cells, immunoregulatory cells and in particular immunoregulatory cells isolated from the spleen. Such immunoregulatory cells include T-cells, such as T-lymphocytes, Nk-cells, B-cells, antigen-regulatory cells, antigen-presenting cells, etc., bone marrow cells. Further examples include liver cells, such as hepatocytes, lymphocytes, macrophages and neutrophiles. Also modified cells, and in particular gene modified cells and gene modified stem cells could benefit from the present invention. Such modified cells have then at least one incorporated gene that encodes a target protein to be expressed in a patient by the gene modified cells. A further variant of cell type is cells to which therapeutic molecules, particles, compounds, viruses, etc. are attached. These attached molecules, particles, compounds, viruses, etc. can then exert an intended function, such as therapeutic function, in the patient body. The embodiments can actually be used in connection with any cell type that one would like to administer to a human or animal body through intravenous injection. Generally, the larger the size of the cells, i.e. cell diameter, including any attachments on the cell surface, the larger quantity of the cells will become taken up by the lungs. Hence, the present embodiments are particularly suitable for usage with such larger cell types.

The cells are generally injected in a fluid or liquid vehicle, i.e. an injection solution. Any of the prior art known and employed such injection solutions that can be used together with living cells can be used according to the embodiments. Examples of known injection solutions that can be used include physiological saline (NaCl (aq)), buffer solutions, such as phosphate buffered saline (PBS) or a citric acid buffer, etc. For instance, dextran sulfate of the embodiments can be dissolved in saline, such as 0.9% NaCl saline, and then buffered with 75 mM citric acid and adjusting the pH to about 5.9 using sodium hydroxide.

In therapeutic treatment of mammals, and especially humans, dextran sulfate and derivates thereof, may be administered alone, but will generally be administered as a pharmaceutical formulation in admixture with a pharmaceutically acceptable adjuvant, diluent or carrier, which may be selected with due regard to the intended route of administration and standard pharmaceutical practice. As has been mentioned above, the dextran sulfate is advantageously added to the injection solutions with the cells prior to injection and is therefore co-administered together with the cells. In such a case, the dextran sulfate will be pre-mixed and incubated together with the cells before the actual injection instance.

The dextran sulfate can be administered according to various embodiments. In a currently preferred embodiment, the dextran sulfate is added to the injection solution together with the cells so that the cells are co-administered intravenously together with the dextran sulfate. In an alternative approach, the cells are intravenously injected separate from an intravenous injection of dextran sulfate dissolved in a suitable solution, such as the same injection solution that has been used for the cells. The dextran sulfate is then advantageously injected at substantially the same site as the cells and preferably immediate prior and/or immediate after the intravenous injection.

In addition or alternatively, the dextran sulfate can be administered in the form of a continuous infusion over time starting at the time of cell injection, shortly following the cell injection or even some time, such as up to one hour or a few hours, prior the cell injection. The infusion can last from, for instance, ten minutes up to a 10 hours, typically from 20 minutes up to 5 hours or even shorter, following the cell injection. Instead of using a continuous infusion the dextran sulfate can administered at multiple separate time instance starting before or at the time of cell injection and then continuing with the separate dextran sulfate administrations up to a few hours following the cell injection.

Co-administration of dextran and the cells can be complemented with administration of dextran sulfate prior to and/or after intravenous co-injection of dextran sulfate and the cells or can be complemented with an infusion of dextran sulfate as disclosed above.

The dextran sulfate, and derivates thereof, may be administered orally, intravenously, intraperitoneally, subcutaneously, buccally, rectally, dermally, nasally, tracheally, bronchially, topically, by any other patenteral route or via inhalation, in the form of a pharmaceutical preparation comprising the active ingredient in a pharmaceutically acceptable dosage form. Preferred administration protocols include intravenous injections and longer infusions.

The dextran sulfate, or derivates thereof, employed according to the embodiments may have a molecular weight from low molecular weight dextran sulfate (LMW-DS), e.g. from a few hundred or thousand Dalton (Da), to high molecular weight dextran sulfate (HMW-DS), generally with an average molecular weight over 500 000 Da, e.g. >1 000 000 Da. The advantageous effect of dextran sulfate is especially prominent for LMW-DS. LMW-DS generally has an average molecular weight of below 20 000 Da, such as below 10 000 Da and e.g. about 8 000 Da, 7 000 Da, 6 000 Da or preferably about 5 000 Da. The average sulfur content for LMW-DS may be about 10 to 25%, such as 15 to 20%, e.g. about 17%, corresponding to about 2 sulfate groups per glucosyl residue. For dextran sulfate with an average molecular weight higher than 20 000 Da, a larger sulfur content could be employed. It is well known to the person skilled in the art that a molecular weight for dextran sulfate is an average weight. This implies that the weights of individual dextran sulfate molecules will be distributed around the average weight.

The dextran sulfate according to the embodiments can be provided as a pharmaceutically acceptable derivative of dextran sulfate. Such pharmaceutically acceptable derivatives include salts and solvates of dextran sulfate, such as a sodium salt of dextran sulfate.

Suitable dose ranges for the dextran sulfate may vary according to the size and weight of the patient, the condition for which the patient is treated, and other considerations. The dextran sulfate can be administered in at a concentration of about 0.1 to 25 mg/kg, preferably 0.5 to 20 mg/kg. Non-limiting examples include 1 to 2.5 mg/kg body weight, such as about 1.5 mg/kg body weight. However, also larger concentrations such as more than 5 mg/kg, such as 5-15 mg/kg are indeed possible.

The relevant dextran sulfate concentration in the administered medicament and the amount of dextran sulfate to administer to a subject can be determined by the physician. As is well known in the art, activated partial thromboplastin time (APTT) is used as a representation of the concentration of dextran sulfate in subject, such as in the blood or plasma of the subject. The APTT can then be used as a safety measure so that the administration of the dextran sulfate of the present invention will not exceed predefined APTT levels that are regarded as safe. For instance, following an administration of dextran sulfate an APTT of about 250 s is safely achieved in human patients. Furthermore, in xeno-transplantation settings, dextran sulfate administrations causing an APTT much higher than 250 s have been employed in the art. In addition, as is presented in the experimental section, infusion of dextran sulfate to achieve an APTT level of 150 s can safely be employed even during long infusion times of about 5 hours.

An aspect of the embodiments relates to dextran sulfate or a pharmaceutically acceptable derivative thereof for use in reducing, preventing or inhibiting pulmonary uptake of intravenously injected or administered cells.

Another aspect relates to a method of reducing, preventing or inhibiting pulmonary uptake of intravenously injected or administered cells comprising administering dextran sulfate or a pharmaceutically acceptable derivative prior to, after and/or at the same time as the intravenously injected cells and/or co-injecting the cells and dextran suflate intravenously.

A related aspect relates to the use of dextran sulfate or pharmaceutically acceptable derivative thereof for the manufacture of a medicament for reducing, preventing or inhibiting pulmonary uptake of intravenously injected cells in a subject.

In the present work it is shown that infused [$^{18}$F]FDG-labelled T-lymphoblasts accumulated in the lungs and that the uptake could be reduced either by changing the mode of administration or by coadminister LMW-DS. A similar adherence of T-lymphocytes to pulmonary tissue after adoptive transfer has been demonstrated in a murine model, where the pulmonary localization of Th1 cells was shown to be partially dependent on intercellular adhesion molecule-1 (ICAM-1) [4].

The large initial uptake in the lungs after intravenous administration seems to be a first-pass effect. Administered T-lymphoblasts were retained in the lungs during the initial pass through the pulmonary system before having the possibility of being distributed throughout the body. The intraarterial mode of infusion was designed to bypass this process thereby allowing a larger amount of T-lymphoblasts to distribute into the rest of the body. The fact that this mode of administration decreased the accumulation in lung supports the first-pass effect hypothesis.

A similar effect was obtained when the T-lymphoblasts were co-administered intravenously together with LMW-DS to a pretreated pig. It is speculated that addition of DS increased the expression of homing and chemokine related ligands in the plasma which in turn upregulated the expression of cell surface receptors like CXCR4, VLA 4, 5 and P-selectin among others leading to enhanced cell mobilization This could explain the shorter pulmonary retention of LMW-DS treated T-lymphoblasts found here.

Tumor specific lymphocytes express a multitude of chemokine and homing receptors and preconditioning of the cells with LMW-DS before adoptive transfer could be a way to enhance homing capabilities of effector cells to peripheral tissue.

There were two different levels of heterogeneity of lung distribution. Firstly, there was a large difference in uptake between the ventral and the dorsal aspects of the lungs. Secondly, the dorsal uptake was not homogenous but instead a considerable percentage of the T-lymphoblasts in the lungs were found in hotspots with high cellular density depending on the mode of administration.

The ventral-dorsal asymmetry was due simply to gravitational effects since the animal is supine during the examination procedure. The second type of heterogeneity, the tendency for the T-lymphoblasts to accumulate in hotspots, increased proportionately with the total lung uptake and may be related to an intrinsic property of the mechanisms of cellular adhesion to lung tissue.

Although the amplitude of lung uptake varied between modes of administration, the kinetics of the washout was similar and concentration dependent. The washout from the lungs was due mainly to T-lymphoblasts leaving the pulmonary tract via the blood-stream by loss of adhesion, assuming retention of [$^{18}$F]FDG in transfused T-lymphoblasts was as high as measured in vitro.

In conclusion, when considering these results in relation to adoptive TIL transfer, the reduction of initial lung uptake results in a larger percentage of cells being distributed into the rest of the body. This is especially important when considering target tissues other than lung metastases, as well as reducing the potential risk for adverse respiratory effects. The protocol can potentially be transferred to the clinical setting with few modifications.

A further aspect of the embodiments therefore relates to a composition comprising dextran sulfate or a pharmaceutically acceptable derivative thereof and tumor infiltrating T-lymphocytes provided in a pharmaceutically acceptable fluid or liquid carrier, such as a pharmaceutically acceptable injection solution. This composition is suitable for use in treatment of metastatic cancer and can therefore be used to manufacture a medicament for treatment of metastatic cancer.

A related aspect therefore relates to a method for treating or reducing metastatic cancer in a subject comprising administering a composition comprising dextran sulfate or a pharmaceutically acceptable derivative thereof and tumor infiltrating T-lymphocytes provided in a pharmaceutically acceptable fluid or carrier to the subject in need for such treatment.

Non-limiting examples of metastatic cancers that the composition can be used treat or inhibit include acute myeloid leukemia (AML), acute lymphoblastic leukemia (ALL), chronic myeloid leukemia (CML), myelodysplastic syndromes (MDS), myeloproliferative disorders (MPD), non-Hodgkin's lymphoma (NHL), Hodgkin's disease (HD), chronic lymphocytic leukemia (CLL), multiple myeloma (MM), juvenile chronic myeloid leukemia, neuroblastoma, ovarian cancer and germ-cell tumors. Other cancer diseases include hairy cell leukemia (HCL), acute promyelocytic leukemia (APL) and other myelomas, leukemias and lymphomas.

Further variants of metastatic cancers can be selected from the examples presented below, including, but not limited to, human sarcomas and carcinomas, e.g. fibrosarcoma, myxosarcoma, liposarcoma, chondrosarcoma, osteogenic sarcoma, chordoma, angiosarcoma, enotheliosarcoma, lymphangiosarcoma, lymphangioendotheliosarcoma, synovioma, mesothelioma, Ewing's tumor, leiomyosarcoma, rhabdomyosarcoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, hemangioblastoma, oligodendroglioma, melanoma, neuroblastoma and retinomblastoma, leukemias, e.g. acute lymphocytic leukemia (ALL), and acute myelocytic leukemia (myeloblastic, promyelocytic, myelomonocytic, monocytic and erytholeukemia), chronic leukemias (chronic myelocytic leukemia, chronic granulocytic leukemia and chronic lymphocytic leukemia), polycythemia vera, lymphoma (Hodgkin's disease and non-Hodgkin's disease), multiple myeloma, Waldenström's macroglobulinemia and heavy chain disease.

Treating or inhibiting a metastatic cancer also encompasses the capability of the composition of reducing the number of metastatic cancer cells and/or reducing the metastatic and/or cell dividing capability of these cancer cells.

EXPERIMENTS

In this study we present a method to monitor transfusion of T-lymphoblasts in vivo in a porcine model by PET-imaging. Porcine T-lymphoblasts were labeled with [$^{18}$F] FDG prior to administration, and the kinetics and biodistribution of the cells was monitored for up to 2 hours. [$^{18}$F]FDG is a functional analogue to glucose, but cannot be metabolized further than the initial phosphorylation by hexokinase and is trapped in the cell cytoplasm. The same concept has been applied by our group to image transplantation of islets of Langerhans in a porcine model [1] and in the clinical setting [2, 3].

In the present work, three modes of administration were compared; intravenous administration with or without co-administration of the complement and coagulatory inhibitor low molecular weight dextran sulphate (LMW-DS), and intraarterial administration.

Material and Methods

Isolation of Porcine T-Lymphoblasts

Spleens from three months old pigs were surgically resected and stored in PBS for immediate preparation. Spleens were cut into smaller fragments and mashed first against a 1 mm steel mesh and a second time with a syringe rubber plunger against a fine nylon mesh. The tissue was resuspended in PBS and the T-lymphoblasts were isolated using Ficoll-Paque (GE-Healthcare Uppsala, Sweden) density gradient centrifugation. All T-lymphoblasts were activated with PHA (1 µg/mL) (Invitrogen, Carlsbad, Calif., USA) to simulate the clinical setting of adoptively transferred tumor infiltrating lymphocytes.

Transfusion of T-lymphoblasts

T-lymphoblasts were suspended in 10-15 mL of PBS and administered over 10 minutes either intravenously into the internal jugular vein (n=5) or intraarterially into the ascending aorta (n=1). Two of the pigs given intravenous administration were pretreated with LMW-DS (4.5 mg/kg) (Apoteket AB, Umeå, Sweden). The T-lymphoblasts were in these two cases co-administered intravenously together with LMW-DS (9 mg/kg, followed by continuous infusion of 7.2 mg/kg/h).

T-lymphoblasts Labeling and In Vitro Retention

[$^{18}$F]FDG ($t_{1/2}$=109.8 min) was prepared according to standard procedures (TRACERlab FxFDG, GE Medical Systems, USA). Cells were incubated with [$^{18}$F]FDG in 7-10 mL PBS for 60 minutes at 37° C. before being washed to remove excess radioactivity.

The retention (the rate of tracer washout through GLUTs after dephosphorylation of [$^{18}$F]FDG-6P) was measured in triplicates at 6 different time points over 120 minutes and the retention half-life was estimated by fitting the data to a mono-exponential curve.

PET-examinations

Six pigs were examined by PET after administration of [$^{18}$F]FDG-labeled T-lymphoblasts. A GE Discovery ST PET/CT scanner (n=3) or a Hamamatsu SHR-7700 scanner (n=3) was used. Dynamic sequences were acquired over the lungs and liver for up to 120 minutes. The kinetic data obtained was expressed as absolute number of cells or the percentage of administered cells. Results are given as averages±SEM.

Results

T-lymphoblast Isolation, Labeling and In Vitro Retention

Up to $10^9$ T-lymphoblasts could be recovered from each spleen with the described method. 500-1000 million T-lymphoblasts were labeled with 10.6-53.1 MBq [$^{18}$F]FDG, with an average of 25.6±6.7 MBq. Porcine T-lymphoblasts had a [$^{18}$F]FDG retention half-life of 319 minutes ($R^2$=0.99). For example, 94% of the label was contained at 30 minutes and 77% at 120 minutes.

Pet-Examination of Transfused T-Lymphoblasts

Following the 6 transfusions, the majority of the initial uptake was found primarily in the lungs. The distribution of labeled T-lymphoblasts in lungs was heterogenous after 30 minutes with parts of the graft located in small hotspots with high cellular density (FIG. 1). The hotspots remained after 120 minutes, although the total uptake had decreased. The major lung uptake was found dorsally and this asymmetry in distribution was found similar for all the modes of administration.

Figure 2:
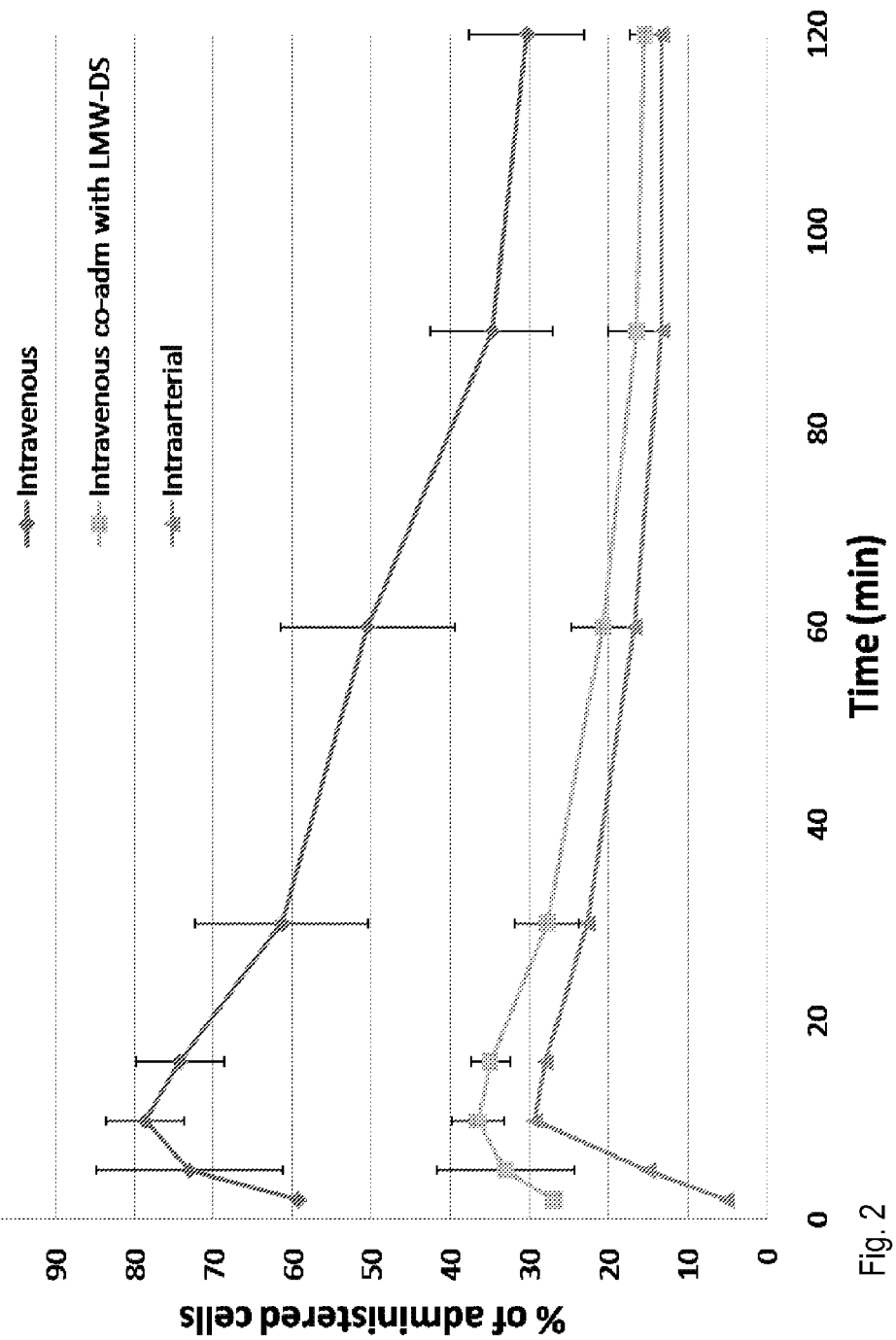
FIG. 2 illustrates lung uptake kinetics (as % of administered T-lymphoblasts) varied between modes of administration. The initial uptake was lower when administering the T-lymphoblasts intraarterially (n=1) or intravenously together with low molecular weight dextran sulfate (LMW-DS) (n=2), compared to after intravenous administration (n=3). Values are given as averages±SEM.

The kinetics of labeled T-lymphoblasts in the lungs following the transfusions is presented in FIG. 2. The relative lung uptake varied between modes of administration, with the highest average uptake after intravenous administration (78.6% of the administered T-lymphoblasts) at completed transfusion. Co-administration of LMW-DS during intravenous administration decreased the uptake to an average of 36.6%. The lung uptake of T-lymphoblasts was lowest (29.4%) following intraarterial administration.

The concentration and total amount of cells trapped in lung tissue could be quantified. Table 1 presents the amount of T-lymphoblasts in the lungs at 30 minutes. Between 80 and up to 635 million cells (16 to 79% of the grafts) was trapped in lung tissue after administration. To quantify the amount of cells trapped in hotspots we defined two levels of density: hotspots with a cellular density over either 250.000 cells/cc (moderate density) or over 500.000 cells/cc (high density).

TABLE 1

T-lymphoblast density and heterogeneity in lungs at 30 minutes varied with mode of administration. The presence of hotspots increased in parallel with the total lung uptake.

| Mode | Administered ($10^6$ cells) | Total amount in lungs ($10^6$ cells) | % of cells in lungs | Moderate density regions ($10^6$ cells) | High density regions ($10^6$ cells) | Max density ($10^6$ cells/cc) |
|---|---|---|---|---|---|---|
| Intravenous | 520 | 411.51 | 79.1 | 184.6 | 170.62 | 2.05 |
| Intravenous | 1000 | 635.43 | 63.5 | 441.79 | 389.55 | 2.23 |

TABLE 1-continued

T-lymphoblast density and heterogeneity in lungs at 30 minutes varied with mode of
administration. The presence of hotspots increased in parallel with the total lung uptake.

| Mode | Administered ($10^6$ cells) | Total amount in lungs ($10^6$ cells) | % of cells in lungs | Moderate density regions ($10^6$ cells) | High density regions ($10^6$ cells) | Max density ($10^6$ cells/cc) |
|---|---|---|---|---|---|---|
| Intravenous | 560 | 172.36 | 30.8 | 101.74 | 67.75 | 0.99 |
| Intraarterial | 560 | 96.68 | 17.3 | 26.08 | 0 | 0.42 |
| LMW-DS | 500 | 81.47 | 16.3 | 27.7 | 0 | 0.49 |
| LMW-DS | 900 | 285.77 | 31.8 | 155.21 | 111.3 | 1.14 |

Between 67-389 Million cells (39-61% of lung uptake) was found in hotspots with high density after intravenous administration. The amount of cells in high density hotspots was lower after coadministration of LMW-DS (0-111 million cells, or 0-39%) and non-existing after intraarterial administration. A similar pattern was seen for moderate density hotspots. The maximal observed density was over 2 million cells/cc.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

REFERENCES

[1] Eich, T., Eriksson, O., Sundin, A., et al., Positron emission tomography: a real-time tool to quantify early islet engraftment in a preclinical large animal model. Transplantation, 2007. 84(7): p. 893-8
[2] Eich, T., O. Eriksson, and T. Lundgren, Visualization of early engraftment in clinical islet transplantation by positron-emission tomography. N Engl J Med, 2007. 356(26): p. 2754-5
[3] Eriksson, O., Eich, T., Sundin, A., et al., Positron Emission Tomography in Clinical Islet Transplantation. Am J Transplant, 2009. 9(12): p. 2816-24
[4] Dixon, A. E., Mandac, J. B., Martin, P. J., et al., Adherence of adoptively transferred alloreactive Th1 cells in lung: partial dependence on LFA-1 and ICAM-1. Am J Physiol Lung Cell Mol Physiol, 2000. 279(3): p. L583-91

The invention claimed is:

1. A cell administering method for reducing pulmonary uptake of intravenously injected cells in a human subject, comprising intravenously injecting cells selected from the group consisting of stem cells, immunoregulatory cells, and bone marrow cells into a human subject and administering dextran sulfate or a pharmaceutically acceptable salt or solvate thereof to the human subject in an amount effective to reduce pulmonary uptake of the cells in the human subject, wherein said dextran sulfate or said pharmaceutically acceptable salt or solvate thereof has an average molecular weight of below 20,000 Da and an average sulfur content of about 10 to 25%.

2. The method according to claim 1, wherein administering said dextran sulfate or said pharmaceutically acceptable salt or solvate thereof comprises intravenously injecting or infusing said dextran sulfate or said pharmaceutically acceptable salt or solvate thereof to said subject.

3. The method according to claim 1, wherein administering said dextran sulfate or said pharmaceutically acceptable salt or solvate thereof comprises administering said dextran sulfate or said pharmaceutically acceptable salt or solvate thereof at a concentration of 0.1 to 25 mg/kg body weight of said subject.

4. The method according to claim 3, wherein administering said dextran sulfate or said pharmaceutically acceptable salt or solvate thereof comprises administering said dextran sulfate or said pharmaceutically acceptable salt or solvate thereof at a concentration of 0.5 to 20 mg/kg body weight of said subject.

5. The method according to claim 4, wherein administering said dextran sulfate or said pharmaceutically acceptable salt or solvate thereof comprises administering said dextran sulfate or said pharmaceutically acceptable salt or solvate thereof at a concentration of 1 to 2.5 mg/kg body weight of said subject.

6. The method according to claim 5, wherein administering said dextran sulfate or said pharmaceutically acceptable salt or solvate thereof comprises administering said dextran sulfate or said pharmaceutically acceptable salt or solvate thereof at a concentration of about 1.5 mg/kg body weight of said subject.

7. The method according to claim 1, wherein administering said dextran sulfate or said pharmaceutically acceptable salt or solvate thereof comprises intravenously co-injecting said dextran sulfate or said pharmaceutically acceptable salt or solvate thereof and said intravenously injected cells.

8. The method according to claim 1, wherein said injected cells are selected from the group consisting of injected autologous cells and injected allogenic cells.

9. The method according to claim 1, wherein said stem cells are selected from the group consisting of hematopoietic stem cells and mesenchymal stem cells.

10. The method according to claim 1, wherein said immunoregulatory cells are selected from the group consisting of T-cells, T-lymphocytes, Nk-cells, B-cells, antigen-regulator cells and antigen-presenting cells.

11. The method according to claim 1, wherein said dextran sulfate or said pharmaceutically acceptable salt or solvate thereof has an average molecular weight of below 10,000 Da.

12. The method according to claim 1, wherein said dextran sulfate or said pharmaceutically acceptable salt or solvate thereof has an average molecular weight selected from the group consisting of 8000 Da, 7000 Da, 6000 Da and 5000 Da.

13. The method according to claim 1, wherein said dextran sulfate or said pharmaceutically acceptable salt or solvate thereof has an average sulfur content of 15 to 20%.

14. The method according to claim 13, wherein said dextran sulfate or said pharmaceutically acceptable salt or solvate thereof has an average sulfur content of about 17%.

15. The method according to claim 1, wherein said pharmaceutically acceptable salt or solvate thereof is a pharmaceutically acceptable salt of dextran sulfate.

16. The method according to claim 1, wherein said dextran sulfate or said pharmaceutically acceptable salt or solvate thereof is injected immediately prior to or immediately after intravenous injection of cells in the subject.

17. The method according to claim 1, wherein the cells are injected in an injection solution comprising one or both of a physiological saline and a buffer solution.

18. The method according to claim 1, wherein the injected cells consist of stem cells, immunoregulatory cells, or bone marrow cells.

19. The method according to claim 1, wherein the injected cells are immunoregulatory cells isolated from the spleen.

* * * * *